(12) United States Patent
Mienie et al.

(10) Patent No.: US 10,125,353 B2
(45) Date of Patent: Nov. 13, 2018

(54) RECOMBINANT THERAPEUTIC GLYCINE N-ACYLTRANSFERASE

(71) Applicant: North-West University, Potchefstroom (ZA)

(72) Inventors: Lodewyk Jacobus Mienie, Potchefstroom (ZA); Alberdina Aike Van Dijk, Potchefstroom (ZA); Christoffel Petrus Stephanus Badenhorst, Potchefstroom (ZA); Rencia Van Der Sluis, Potchefstroom (ZA)

(73) Assignee: North-West University, Potchefstroom (ZA)

( * ) Notice: Subject to any disclaimer, the term of this patent is extended or adjusted under 35 U.S.C. 154(b) by 0 days.

(21) Appl. No.: 15/274,234

(22) Filed: Sep. 23, 2016

(65) Prior Publication Data

US 2017/0073650 A1    Mar. 16, 2017

Related U.S. Application Data

(62) Division of application No. 13/818,481, filed as application No. PCT/IB2011/053721 on Aug. 24, 2011.

(30) Foreign Application Priority Data

Aug. 24, 2010  (ZA) ................................ 2010/06021

(51) Int. Cl.
  *C12N 9/10*   (2006.01)
  *C12P 21/02*  (2006.01)

(52) U.S. Cl.
  CPC ............ *C12N 9/1029* (2013.01); *C12P 21/02* (2013.01); *C12Y 203/01013* (2013.01)

(58) Field of Classification Search
  None
  See application file for complete search history.

(56) References Cited

U.S. PATENT DOCUMENTS

2005/0064545 A1    3/2005  Demarco et al.
2006/0035221 A1    2/2006  Bergmann et al.
(Continued)

OTHER PUBLICATIONS

Wajner et al., "Disruption of mitochondrial homeostasis in organic acidurias: insights from human and animal studies", Journal of Bioenergetics and Biomembranes, vol. 43, pp. 31-38, 2011.*

(Continued)

*Primary Examiner* — Richard C Ekstrom
(74) *Attorney, Agent, or Firm* — Schwegman Lundberg & Woessner, P.A.

(57) ABSTRACT

This invention relates to a method of producing a recombinant enzyme, more particularly, this invention relates to a method of producing water soluble enzymatically active recombinant glycine N-acyltransferase (GLYAT (E.G. 2.1.3.13)), including the steps of providing a suitable expression host; preparing a vector including a gene for expressing GLYAT in the expression host to form an expression plasmid; transforming the host with the expression plasmid to form an expression system; expressing the GLYAT gene in the expression system; and separating the expressed GLYAT from the expression system.

9 Claims, 6 Drawing Sheets

(56) References Cited

U.S. PATENT DOCUMENTS

| | | |
|---|---|---|
| 2010/0011456 A1 | 1/2010 | Mathur et al. |
| 2013/0224175 A1 | 8/2013 | Mienie et al. |
| 2016/0090577 A1 | 3/2016 | Venkateswaran et al. |

OTHER PUBLICATIONS

"U.S. Appl. No. 13/818,481, Advisory Action dated Oct. 2, 2015", 5 pgs.

"U.S. Appl. No. 13/818,481, Examiner Interview Summary dated Apr. 14, 2016", 3pgs.

"U.S. Appl. No. 13/818,481, Final Office Action dated Jun. 5, 2015", 12 pgs.

"U.S. Appl. No. 13/818,481, Final Office Action dated Jun. 23, 2016", 10 pgs.

"U.S. Appl. No. 13/818,481, Non Final Office Action dated Oct. 22, 2014", 17 pgs.

"U.S. Appl. No. 13/818,481, Non Final Office Action dated Dec. 4, 2015", 9 pgs.

"U.S. Appl. No. 13/818,481, Preliminary Amendment filed Feb. 22, 2013", 7 pgs.

"U.S. Appl. No. 13/818,481, Response filed Apr. 21, 2015 to Non Final Office Action (dated Oct. 22, 2014", 10 pgs.

"U.S. Appl. No. 13/818,481, Response filed Jun. 3, 2016 to Non Final Office Action dated Dec. 4, 2015", 8 pgs.

"U.S. Appl. No. 13/818,481, Response filed Aug. 31, 2015 to Final Office Action dated Jun. 5, 2015", 9 pgs.

"U.S. Appl. No. 13/818,481, Response filed Sep. 29, 2014 to Restriction Requirement dated Jul. 29, 2014", 6 pgs.

"U.S. Appl. No. 13/818,481, Restriction Requirement dated Jul. 29, 2014", 6 pgs.

"International Application Serial No. PCT/IB2011/053721, International Search Report dated Mar. 14, 2012", 4 pgs.

Badenhorst, et al., "Bacterial expression and elucidation of the catalytic mechanism of glycine N-acyltransferase", Journal of Inherited Metabolic Disease, vol. 33, (2010).

Badenhorst, et al., "Enzymatic characterization and elucidation of the catalytic mechanism of a recombinant bovine glycine N-acyltransferase", Drug Metabolism and Disposition, vol. 40, No. 2, (2012), 346-352.

Cardenas, et al., "Genetic polymorphisms of glycine N-acyltransferase (GLYAT) in a French Caucasian population", Xenobiotica, vol. 40, No. 12, (2010), 853-861.

Dempsey, et al., "Expression, purification, and characterization of mouse glycine N-acyltransferase in *Escherichia coli*", Protein Expression and Purification, vol. 97, (2014), 23-28.

Kelley, M., et al., "Isolation and characterization of mitochondrial acyl-CoA: glycine N-acyltransferases from kidney", J Biochem Toxicol., 8(2), (Jun. 1993), 63-9.

Kelley, M., et al., "The effects of ions on the conjugation of xenobiotics by the aralkyl-CoA and arylacetyl-CoA N-acyltransferases from bovine liver mitochondria", J Biochem Toxicol., 5(2), (Summer, 1990), 125-35.

Knights, K M, et al., "Enzymology of Amino Acid Conjugation Reactions", Elsevier Reference Module in Biomedical Sciences, (2014), 1-21.

Matsuo, et al., "Designation of enzyme activity of glycine-N-acyltransfease family genes and depression of glycine-N-acyltransferase in human hepatocellular carcinoma", Biochemical and Biophysical Research Communications, vol. 420, (2012), 901-906.

Mawal, Y. R, et al., "Purification to homogeneity of mitochondrial acyl coa:glycine n-acyltransferase from human liver", Biochem Biophys Res Commun., 205(2), (Dec. 15, 1994), 1373-9.

Van, Der Sluis, et al., "Characterization of the influence of genetic variations on the enzyme activity of a recombinant human glycine N-acyltransferase", Gene, vol. 515, (2013), 447-453.

Van Der Westhuizen, F. H, "*Homo sapiens* putative glycine-N-acyltransferase mRNA, complete cds", Retrieved from NCBI accession No. GenBank AF023466, (Oct. 21, 1997).

Vessey, et al., "Determination of the sequence of the aralkyl acyl-CoA:amino acid N-acyltransferase from bovine liver mitochondria", Journal of Biochemical Toxicology, vol. 11, No. 5, (1996), 211-215.

Vetting, et al., "Structure and functions of the GNAT superfamily of acetyltransferases", Archives of Biochemistry and Biophysics, vol. 433, (2005), 212-226.

Waluk, D. P, et al., "Identification of glycine N-acyltransferase-like 2 (GLYATL2) as a transferase that produces N-acyl glycines in humans.", FASEB J., 24(8), (Aug. 2010), 2795-803.

Yamamoto, et al., "Genetic polymorphisms of glycine N-acyltransferase in Japanese individuals", Drug Metabolism and Pharmacokinetics, vol. 24, No. 1, (2009), 114-117.

Zhang, Haoxing, et al., "Molecular Cloning and Characterization of a Novel Human Glycine-N-acyltransferase Gene GLYATL1, Which Activates Transcriptional Activity of HSE Pathway", International Journal of Molecular Sciences, (2007), 433-444.

Bendtsen, Jannick Dyrløv, et al., "Prediction of twin-arginine signal peptides", BMC bioinformatics 6.1, (2005), 167.

Mukhopadhyay, Abhijit, et al., "Delivery of drugs and macromolecules to mitochondria", Advanced drug delivery reviews 59.8, (2007), 729-738.

\* cited by examiner

RECOMBINANT THERAPEUTIC GLYCINE N-ACYLTRANSFERASE

PRIORITY APPLICATIONS

This application is a Continuation of U.S. application Ser. No. 13/818,481, filed 13 May 2013, which is a U.S. National Stage Filing under 35 U.S.C. 371 from International Application No. PCT/IB2011/053721, filed on 24 Aug. 2014, and published as WO2012/025895 on 1 Mar. 2012, which claims the benefit of priority of South African Application No. 2010/06021, filed on 24 Aug. 2010; which applications and publication are incorporated herein by reference in their entirety.

INTRODUCTION AND BACKGROUND TO THE INVENTION

This invention relates to a method of producing a recombinant enzyme. More particularly, this invention relates to a method of producing water soluble enzymatically active recombinant glycine N-acyltransferase (GLYAT (E.C. 2.3.1.13)).

Detoxification of toxic metabolites by the human body is an essential physiological process. The detoxification process decreases the toxicity of several endogenous metabolites, such as steroid hormones, and exogenous toxins, which could include compounds in food or industrial chemicals.

The detoxification process is divided into three main phases. Phase I detoxification activates metabolites by adding functional groups. The activated compounds generated by phase I detoxification are often more reactive and toxic than the original metabolites, and are further processed by phase II detoxification systems. In phase II detoxification, a range of conjugation reactions serve to make the activated compounds less toxic and more soluble, for excretion in the urine and bile. Phase III detoxification involves the elimination of toxins from cells.

Organic acidemias are a group of metabolic disorders caused by dysfunctional organic acid metabolism. The deficiency of certain metabolic enzymes causes the accumulation of acids which are not normally present in high levels in the human body. There are several known organic acidemias, with methylmalonic acidemia, propionic acidemia, isovaleric acidemia, glutaric aciduria, and maple syrup urine disease being some common examples.

Isovaleric acidemia is an autosomal recessive disorder. It is caused by a deficiency of isovaleryl coenzyme A dehydrogenase. A deficiency of this enzyme results in accumulation of intermediates of leucine catabolism, including isovaleric acid, 3- and 4-hydroxyisovaleric acid, isovalerylcarnitine and isovalerylglycine.

Isovalerylglycine is formed when isovaleric acid conjugates to glycine by glycine N-acyltransferase (GLYAT). The isovalerylglycine is less toxic than isovaleric acid, indicating that glycine conjugation is of critical importance in the treatment of isovaleric acidemia.

Urea cycle disorder is a genetic disorder caused by an enzyme deficiency in the urea cycle responsible for eliminating ammonia from the blood stream. In urea cycle disorders, nitrogen accumulates in the form of ammonia resulting in hyperammonemia which ultimately causes irreversible brain damage, coma and/or death.

A known method for enhancing glycine conjugation capacity in individuals suffering from organic acidemias is the administration of glycine supplements. Assays on liver samples have however shown that there is great variability in the glycine conjugation capacity in humans.

It is therefore evident that a means of augmenting the natural capacity for glycine conjugation would not only be beneficial to the general health of humans but may further present as an alternative therapeutic strategy for individuals affected by organic acidemias, urea cycle disorders, aminoacidurias, and exposure to some xenobiotic chemicals.

GLYAT is an enzyme responsible for the phase II detoxification of several toxic organic acids by means of conjugation to glycine. Several toxic compounds, both xenobiotic and endogenously derived metabolites, are detoxified by conjugation to glycine. In addition to GLYAT's role in the detoxification of benzoic acid, the enzyme is also important in the management of certain inborn errors of metabolism.

To date, no system for the bacterial expression and purification of an enzymatically active recombinant GLYAT has been reported.

A disadvantage associated with the lack of a system for expression of an enzymatically active recombinant GLYAT is that there is no commercially viable product currently available for directly improving the capacity of the glycine-conjugation detoxification system, particularly in the case of patients with metabolic disorders.

OBJECTS OF THE INVENTION

It is accordingly an object of the present invention to provide a novel method of producing water soluble enzymatically active recombinant glycine N-acyltransferase (GLYAT) enzyme and to provide GLYAT produced with such a method.

It is a further object of the invention to provide use of a pharmaceutically effective amount of GLYAT in a method of enhancing detoxification and for treating and/or preventing metabolic disorders in mammals.

It is yet another object of the invention to provide a method of enhancing detoxification in mammals and for treating and/or preventing metabolic disorders with which the aforesaid disadvantage may be overcome or at least minimised.

SUMMARY OF THE INVENTION

According to a first aspect of the invention there is provided a method of producing water soluble enzymatically active recombinant glycine N-acyltransferase (GLYAT) including the steps of:
  providing a suitable expression host;
  preparing a vector including a gene for expressing GLYAT in the expression host to form an expression plasmid;
  transforming the host with the expression plasmid to form an expression system;
  expressing the GLYAT gene in the expression system; and
  separating the expressed GLYAT from the expression system.

Further according to the invention the step of separating the expressed GLYAT from the expression system may include the steps of separating the water soluble fraction of the expression system from the insoluble material and concentrating or lyophilising the separated GLYAT.

Further according to the invention the expression host may be selected from the group consisting of eukaryotic systems, including yeast cell expression-, insect cell expression- and mammalian cell expression systems; prokaryotic systems, including *Escherichia coli* and *Bacillus subtilis* and archaeon systems.

Further according to the invention the method includes a further step of combining the separated expressed GLYAT with glycine.

According to a second aspect of the invention there is provided water soluble enzymatically active recombinant GLYAT prepared in accordance with the first aspect of the invention.

According to a third aspect of the invention there is provided a medicament comprising water soluble enzymatically active recombinant GLYAT prepared in accordance with the first aspect of the invention.

According to a fourth aspect of the invention there is provided use of a pharmaceutically effective amount of water soluble enzymatically active recombinant GLYAT prepared in accordance with the first aspect of the invention in a method of:

improving the capacity of a glycine-conjugation detoxification system;

enhancing detoxification; or treating and/or preventing metabolic disorders and acute or chronic poisoning with compounds such as xylene or aspirin in mammals.

According to a fifth aspect of the invention water soluble enzymatically active recombinant GLYAT may be used in a method of:

improving the capacity of a glycine-conjugation detoxification system;

enhancing detoxification; or treating and/or preventing metabolic disorders and acute or chronic poisoning with compounds such as xylene or aspirin, in mammals by administering to a mammal in need thereof a biologically effective amount of between 0.1 mg and 160 mg of water soluble enzymatically active recombinant GLYAT per kilogram of body mass depending on the demand for increased glycine conjugation.

According to a sixth aspect of the invention there is provided use of a pharmaceutically effective amount of water soluble enzymatically active recombinant GLYAT prepared in accordance with the method of the first aspect of the invention in a method of manufacturing a medicament for use in:

improving the capacity of a glycine-conjugation detoxification system;

enhancing detoxification; or treating and/or preventing metabolic disorders and acute or chronic poisoning with compounds such as xylene or aspirin in mammals.

Further according to the invention the metabolic disorders may be any one or more of the conditions selected from the group consisting of organic acidemias selected from propionic acidemia, isovaleric acidemia and glutaric aciduria, aminoacidurias selected from maple syrup urine disease and hyperglycinemia; and urea cycle disorder.

According to the seventh aspect of the invention there is provided a medicament prepared from water soluble enzymatically active recombinant GLYAT in accordance with the first aspect of the invention together with at least one inert pharmaceutically acceptable carrier or diluents in a dosage form selected from the group consisting of tablets; capsules; suspension; syrup; intradermal-; intramuscular-; intravenous-; and subcutaneous injection.

The water soluble enzymatically active recombinant GLYAT may be administered by intravenous injection (IV) with a preparation of the enzyme in a form that is targeted to the desired sub-cellular compartments. Alternatively, water soluble enzymatically active recombinant GLYAT may be administered by using a GLYAT enzyme fused to the membrane permeating TAT (transactivator of transcription) peptide, allowing the recombinant enzyme to effectively cross cell membranes to reach the desired mitochondrial matrix. Further alternatively, water soluble enzymatically active recombinant GLYAT may be administered by using a colloidal system that contains unique and stable lipid-based submicron- and micron-sized structures.

Further according to the invention the step of administering the biologically effective amount of water soluble enzymatically active recombinant GLYAT may include the further step of administering the water soluble enzymatically active recombinant GLYAT in combination with glycine to further stimulate glycine conjugation capacity.

BRIEF DESCRIPTION OF THE FIGURES

The invention will now be described further, by way of example only, with reference to the accompanying figures wherein.

DESCRIPTION OF PREFERRED
EMBODIMENTS OF THE INVENTION

According to a preferred embodiment of the invention there is provided a method for producing water soluble enzymatically active recombinant glycine N-acyltransferase (GLYAT).

The method includes the steps of providing a suitable expression host providing a GLYAT expressing gene; preparing a vector including a gene for expressing GLYAT in the expression host to form an expression plasmid; transforming the host with the expression plasmid to form an expression system; expressing the GLYAT in the expression system; separating the expressed GLYAT from the expression system; and combining the separated expressed GLYAT with glycine.

The expression host is selected from the group consisting of eukaryotic systems, including yeast cell expression, insect cell expression and mammalian cell expression, prokaryotic systems, including *Escherichia coli* and *Bacillus subtilis* and archaeon systems. It was found that *Escherichia coli* (*E. coli*) provided a particularly suitable host.

Figure 1:
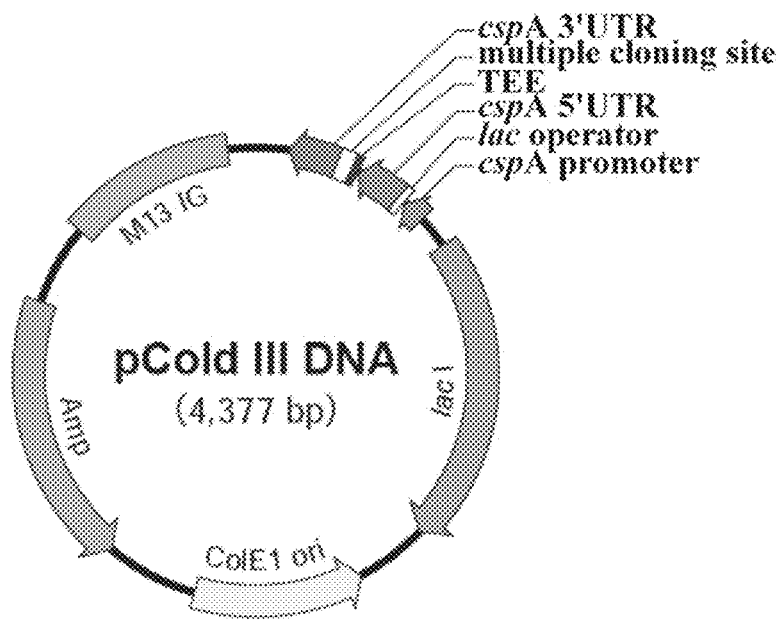
FIG. 1: is a diagram illustrating the pColdIII expression vector used for expression of bovine GLYAT in accordance with a preferred embodiment of the invention.

The gene encoding bovine GLYAT was isolated from bovine liver RNA and cloned, by means of reverse transcription and polymerase chain reaction (PCR) amplification, into a pColdIII expression vector (as illustrated in FIG. 1). The pColdIII expression vector allows for the expression of a protein in *E. coli* at 15 degrees Celsius, which enhances the expression of soluble, enzymatically active recombinant proteins.

Various other vectors could also be used for the expression of recombinant human and bovine GLYAT, or other GLYAT variants, in eukaryotic, prokaryotic and archaeon expression hosts.

In order to obtain a suitable vector, a histidine-tag (His-tag) is attached to the C-terminus of the gene. In the alternative to C-terminal histidine tags, tags are selected from the group consisting of N-terminal hexahistidine tags, maltose binding protein (MBP), giutathione S-transferase, GST tags and Strep-Tag II.

GLYAT is alternatively expressed without any purification tags, and separated from the proteins of the expression host by utilising known protein purification strategies. Owing to the fact that GLYAT is a nucleotide-cofactor binding enzyme, it may further alternatively be purified by affinity chromatography.

Example 1

Recombinant Bovine GLYAT

Recombinant bovine GLYAT was cloned into a set of three modified pColdIII (pColdIII-E, pColdIII-A and pColdIII-EH) expression vectors encoding C-terminal histidine tags.

In order to clone the coding sequence into the expression vectors, the sequence is amplified through polymerase chain reaction (PCR) using primers containing Ndel and Xhol restriction enzyme sites to facilitate directional cloning. The PCR reaction mixtures contained 1× Takara ExTaq buffer, 10 nmol of each dNTP, 25 pmol of each primer, approximately 50 ng of template DNA and 2 units of Takara ExTaq polymerase, in a final volume of 50 µl. Thermal cycling conditions were 94 degrees Celsius for 1 min, then 30 cycles of 94 degrees Celsius for 30 seconds, 70 degrees Celsius for 30 seconds, and 72 degrees Celsius for 1 minute, followed by a final extension at 72 degrees Celsius for 10 minutes.

Figure 2:
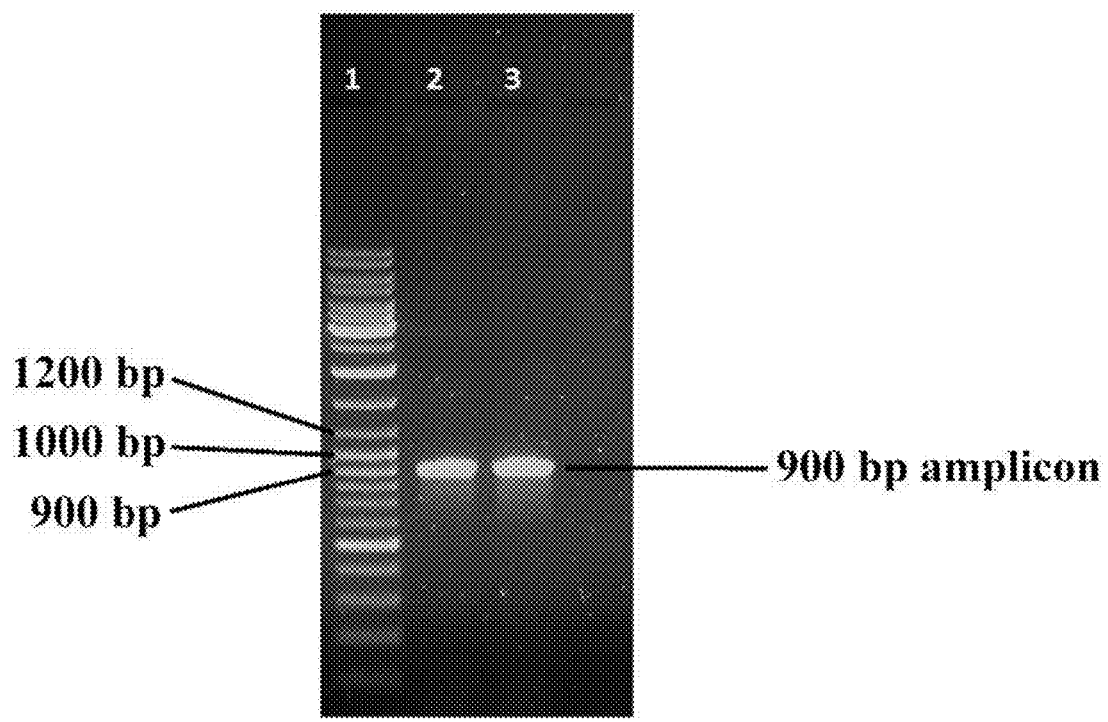
FIG. 2: is a polymerase chain reaction (PCR) amplification of an open reading frame (ORF) encoding bovine GLYAT from a plasmid into which the ORE encoding bovine GLYAT had already been cloned (the original PCR amplification and cloning were performed using cDNA from bovine liver)

After transforming *E. coli* with an expression plasmid containing a recombinant GLYAT coding sequence, colonies were screened for desired recombinant plasmids using either restriction analysis or PCR amplification. A colony was considered to be positive if an excised fragment of approximately 900 bp could be seen on an agarose gel, as illustrated in FIG. 2.

The recombinant protein was purified using a nickel affinity purification process. Upon passage through a resin with nickel ions immobilised onto it, the histidine tags fused to the recombinant GLYAT binds tightly to the column matrix, by forming coordinate bonds with the nickel ions immobilised on its surface. This enables most other proteins to be washed from the column, while the histidine tagged GLYAT remains bound. The tagged protein was eluted with a buffer containing a high concentration of imidazole, which displaced the coordinate bonds between the histidine residues and nickel ions, resulting in a partially purified recombinant protein.

Figure 3:
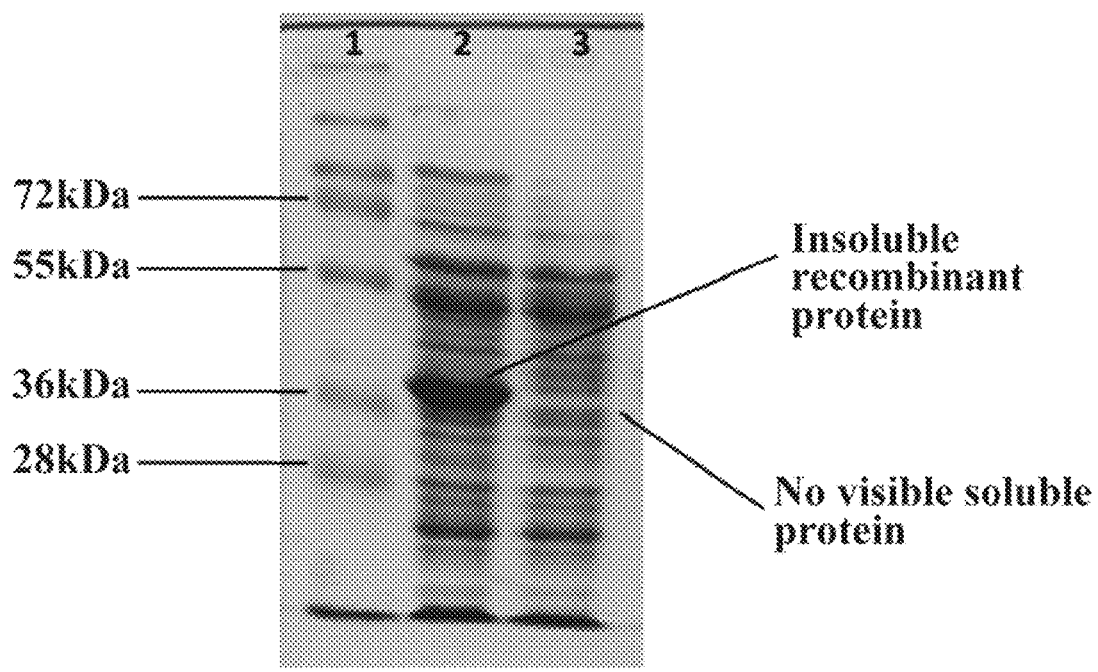
FIG. 3: is a sodium dodecyl sulfate (SDS) polyacrylamide gel electrophoretogram (PAGE) illustrating the total and soluble fractions of the expression of recombinant bovine GLYAT (lanes 2 and 3, respectively)

Referring to FIG. 3, a sodium dodecyl sulfate (SDS) polyacrylamide gel electrophoretogram (PAGE) was used to analyse the expression of bovine GLYAT from the pColdIII vector. The proteins were visualised by staining with Coomassie brilliant blue. Lane 2 illustrates the total fraction of expressed protein and lane 3 illustrates the soluble fraction of bacterial lysate; with the soluble recombinant GLYAT expressed not being clearly visible on the background of bacterial proteins.

Figure 4:
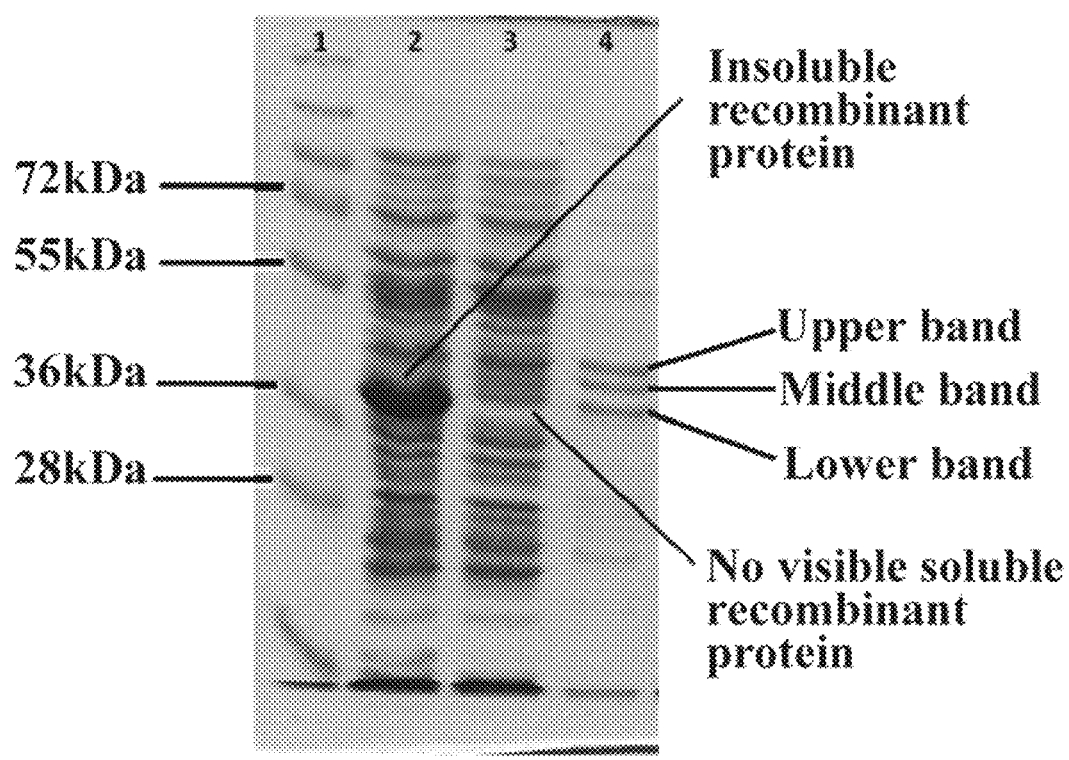
FIG. 4: is an SDS-PAGE analysis illustrating the total and soluble fractions of the expression of recombinant bovine GLYAT (lanes 2 and 3, respectively) as well as the partially purified enzyme (nickel affinity chromatography) in lane 4.

Referring to FIG. 4, recombinant bovine GLYAT was expressed from pColdIII with a C-terminal histidine tag. The soluble fraction was passed through a nickel affinity purification column, to purify the tagged recombinant GLYAT enzyme. The levels of soluble recombinant bovine GLYAT expressed were low, therefore, the final eluate of the purification was significantly concentrated. SDS-PAGE analysis revealed the total fraction of expressed protein in lane 2. Lane 3 represents the soluble fraction of the recombinant GLYAT with no significant amount of soluble recombinant GLYAT being visible against the background of bacterial proteins. Lane 4 illustrates the partially purified enzyme as a result of the nickel-affinity purification. The lower band indicates the active form of the GLYAT enzyme.

Figure 5:
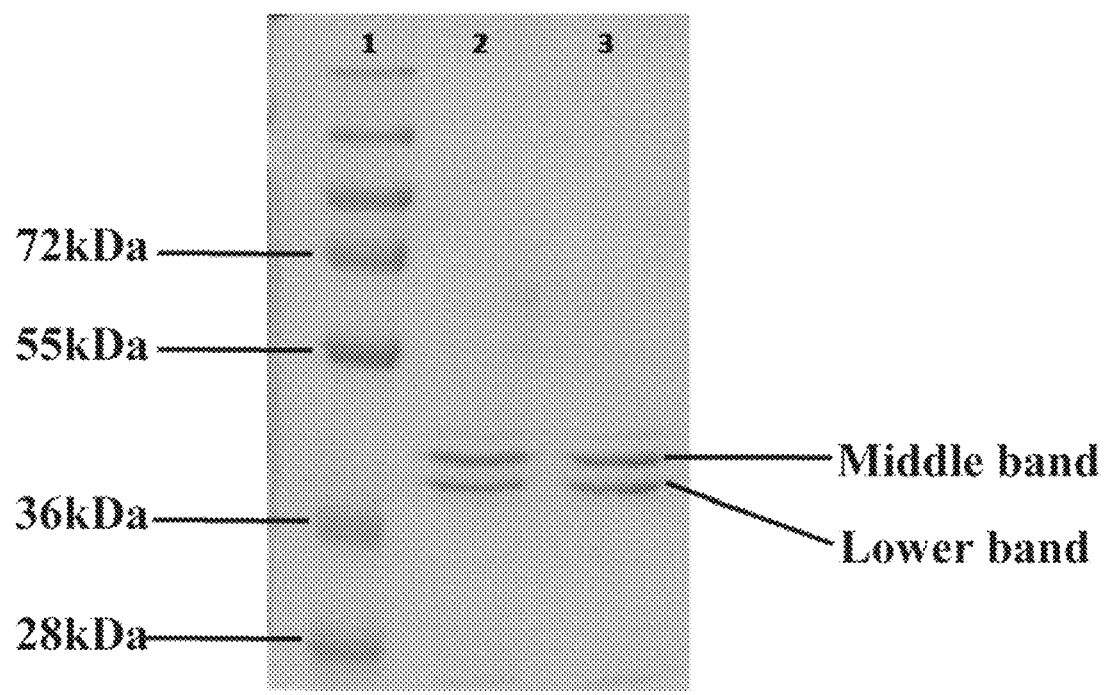
FIG. 5: is an SDS-PAGE analysis illustrating the enzyme after partial purification using nickel affinity chromatography (in this purification 20 mM imidazole was added to the wash purification buffers)

Referring to FIG. 5, 20 mM imidazole was added to the column wash buffers of the purification kit. The use of imidazole in the buffers resulted in the majority of the previously co-purifying proteins being lost. The lower bands, in FIG. 5, represent the enzymatically active bovine GLYAT and an unknown protein.

It was found that the recombinant bovine GLYAT enzyme, prepared in accordance with the invention, has similar biochemical characteristics to the GLYAT enzyme purified from bovine liver.

Example 2

Recombinant Human GLYAT

The nucleotide sequence encoding the human GLYAT sequence was synthesised and cloned into the pET32 expression vector.

The pET32 expression vector enables the expression of human GLYAT with an N-terminal hexahistidine tag and an N-terminal Trx-tag, which respectively facilitates the purification and correct folding of the enzyme.

The expression vector encoding human GLYAT was transformed into Origami expression cells. The cells were also transformed with the pGro7 vector from Takara, which resulted in co-expression of the GroES and GroEL chaperone proteins. Chaperone proteins aid in the correct folding of proteins and increase the yield of soluble recombinant enzymes.

The Origami cells containing the plasmids for expression of recombinant human GLYAT and the chaperone proteins were grown in liquid culture. It was found that the optimal expression of soluble GLYAT occurs in the absence of IPTG (Isopropyl β-D-1-thiogalactopyranoside), thus allowing GLYAT to be expressed at slow basal rate as oppose to the known method of inducing the fusion protein with IPTG to express.

After expression, cells were harvested by means of centrifugation, and lysed using an optimised native lysis buffer containing 300 mM NaCl, 50 mM phosphate buffer, pH 8.0, 10% glycerol, 1% Triton-X, lysozyme, and protease inhibitors. The cell lysates were clarified, using centrifugation at 10 000 g for 30 minutes to remove the insoluble material and passed through Protino nickel affinity purification columns to selectively bind the hexahistidine tagged enzymes. The columns were washed, and the purified protein eluted in a final volume of 3 ml.

Figure 6:
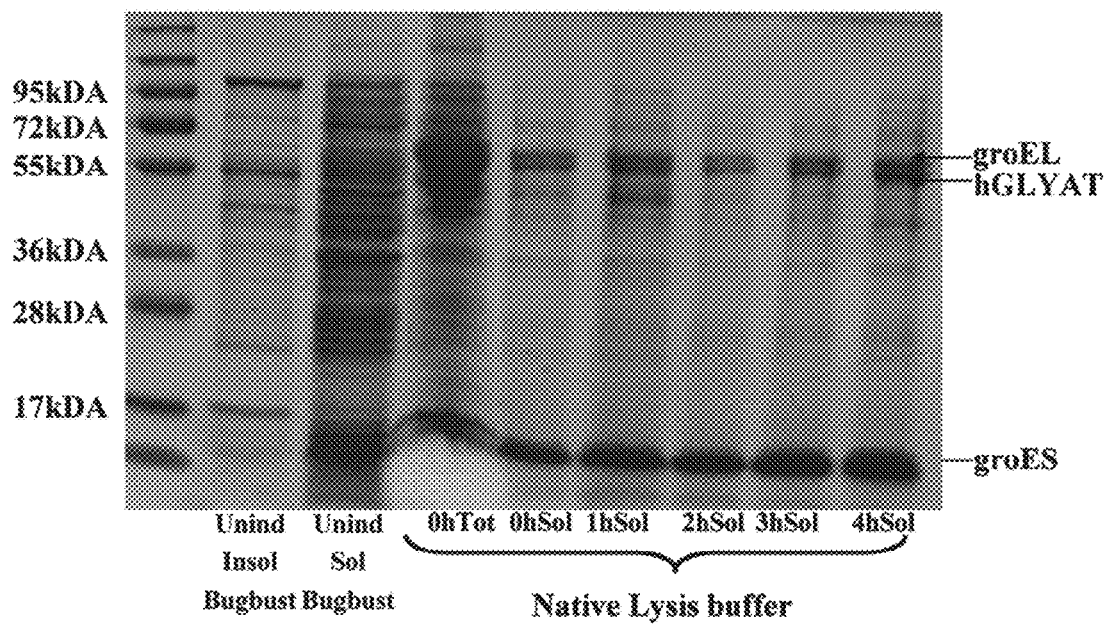
FIG. 6: is an SDS-PAGE analysis illustrating the expression of a soluble recombinant human GLYAT gene (lanes 4 to 9), with an N-terminal fusion of the hexahistidine tag and Trx-tag.

Referring to FIG. 6, soluble recombinant human GLYAT was expressed with an N-terminal hexahistidine-Trx-fusion tag. Lane 1 contains molecular size markers, Lanes 2 and 3 contain the insoluble and soluble fractions, respectively, of a culture, of which the cells were lysed using the BugBuster protein extraction reagent. It was found that this lysis reagent was not suitable for the extraction of recombinant human GLYAT, as no soluble recombinant human GLYAT was visible.

As an alternative, the optimised native lysis buffer was used to isolate the protein from cultures expressing from 0 hours to 4 hours, and the soluble fractions were loaded in lanes 5 to 9. The hexahistidine-Trx-GLYAT fusion protein is indicated by the arrow, in the 55 kDa range.

Figure 7:
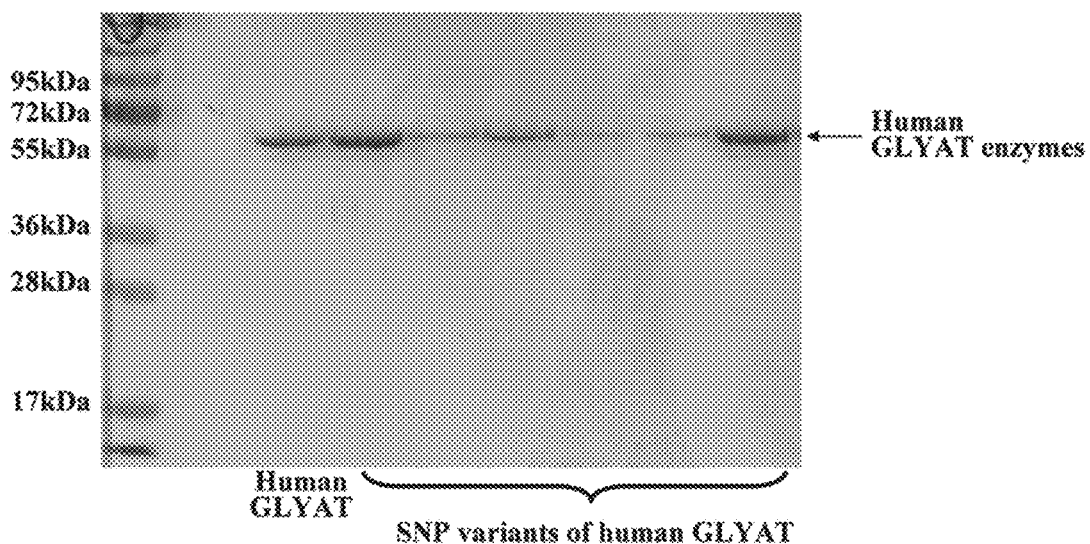
FIG. 7: is an SDS-PAGE analysis illustrating the nickel-affinity purification of wild-type recombinant human GLYAT (lane 3) and single nucleotide polymorphism (SNP) variants of human GLYAT (lanes 4 to 9)

Referring to FIG. 7, the soluble recombinant human GLYAT fusion proteins are purified by means of nickel-affinity chromatography, using Protino Ni-TED columns. Lane 1 contains molecular weight markers, and lane 2 is empty. Lane 3 contains the wild-type recombinant human GLYAT fusion protein, after purification. Lanes 4 to 9 contain purified recombinant human GLYAT, as prepared in accordance with the invention, fusion proteins, of the known single nucleotide polymorphism (SNP) variations of the gene.

Figure 8:
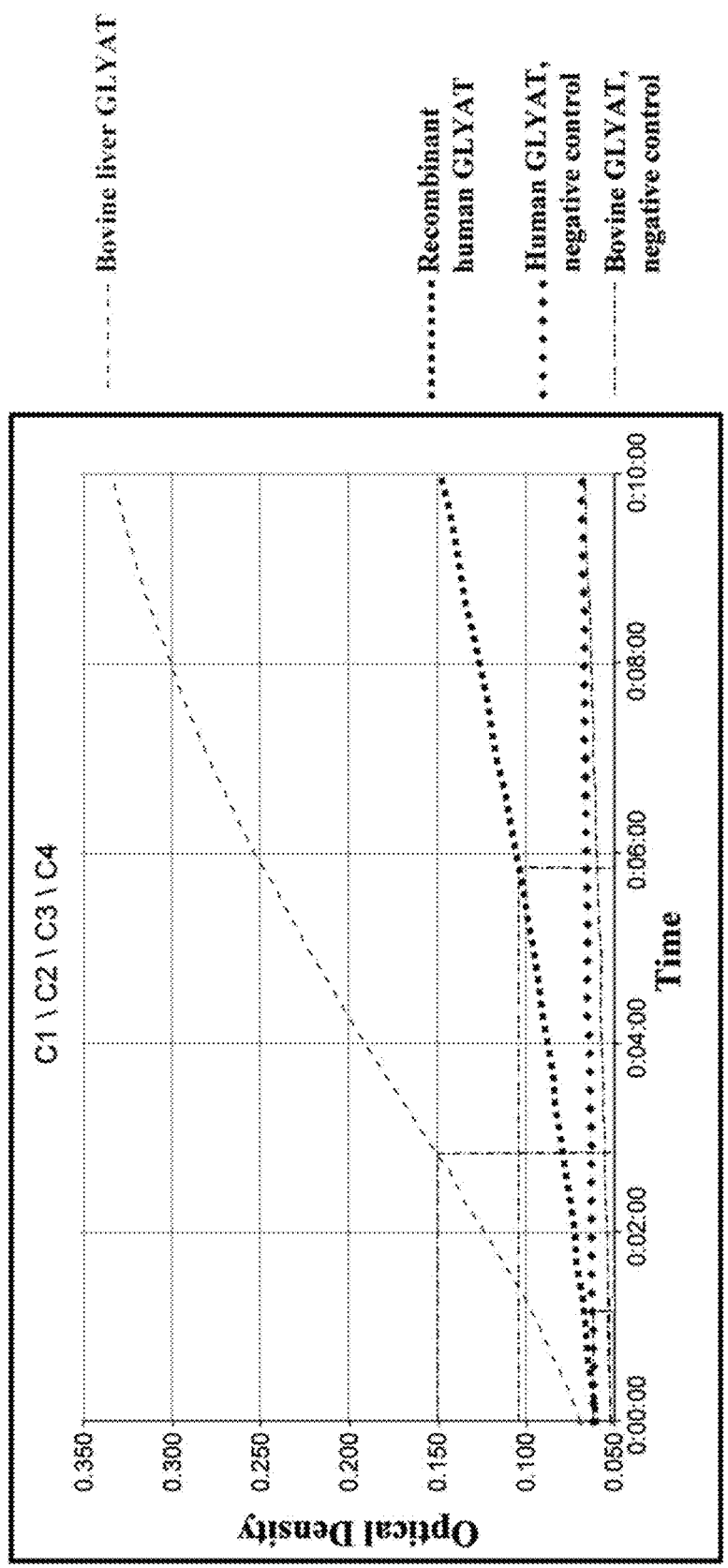
FIG. 8: is a spectrophotometric assay illustrating enzyme activity of recombinant human GLYAT and bovine liver GLYAT in the presence and absence of glycine.

Referring to FIG. 8, the resultant enzyme preparation was assayed for enzyme activity using the spectrophotometric assay for GLYAT. In the assay, bovine GLYAT is used as a positive control. Reactions without glycine were run as negative controls illustrating that the enzyme activity observed is glycine dependent. The recombinant human GLYAT illustrated an increase in optical density (OD) at 412 nm confirming the enzyme activity of recombinant human GLYAT, prepared in accordance with the invention, in the presence of glycine.

In addition to using a recombinant therapeutic GLYAT enzyme in the above described manner, it is possible that novel forms of the GLYAT enzyme may be obtained by rational and semi-rational enzyme engineering strategies, and these may alternatively be used for their specialised functions. Qualities of the GLYAT enzyme that may be subjected to modification by enzyme engineering strategies include catalytic rate, substrate specificity, stability, immunological aspects, and optimal substrate concentration.

There are six known natural SNP (single nucleotide polymorphism) variants of human GLYAT and site-directed mutagenesis was used to generate these variant coding sequences from the wild-type sequence. It was found that of the six SNP variants, two have higher enzyme activity than the wild-type GLYAT, and the rest have much lower activity than the wild-type GLYAT. It is to be expected that there would be clear benefits associated with the use of variants with increased catalytic rate, for example.

Further Findings and Analysis

In use, a pharmaceutically effective amount of 0.1 mg to 160 mg of the recombinant GLYAT enzyme per kilogram of body weight, depending on the nature and extent of the metabolic disorder, is administered to a patient in need thereof by way of intravenous injection (IV) with a preparation of the enzyme in a form targeting the desired subcellular compartments. Alternatively, the prepared recombinant GLYAT enzyme is administered by using a TAT (transactivator of transcription) peptide to act as a membrane permeating agent, which will allow the recombinant enzyme to effectively cross cell membranes to reach the desired mitochondrial matrix. Further alternatively, the prepared recombinant GLYAT enzyme is administered using a colloidal system that contains unique and stable lipid-based submicron- and micron-sized structures to enhance detoxification and to treat and/or prevent metabolic disorders and acute or chronic poisoning with compounds such as xylene or aspirin in mammals.

The metabolic disorders may be any one or more of the conditions selected from the group consisting of organic acidemias selected from propionic acidemia, isovaleric acidemia and glutaric aciduria; aminoacidurias selected from maple syrup urine disease, and hyperglycinemia, and urea cycle disorder.

The recombinant GLYAT is further alternatively formulated into any one of the following dosage forms comprising tablet; capsule; suspension; syrup; intradermal-; intramuscular-; intravenous-; and subcutaneous injection.

A medicament prepared from the recombinant GLYAT in combination with glycine is used to directly improve the capacity of the glycine-conjugation detoxification system in the treatment of patients exposed to chemical and industrial solvents and in the emergency treatment of acute aspirin poisoning. Glycine conjugation of several organic acids is enhanced by the use of a recombinant therapeutic GLYAT enzyme.

It will be appreciated that in terms of the invention, variations in details in providing a novel method of producing a recombinant enzyme and more particularly relating a novel method of producing a water soluble enzymatically active recombinant glycine N-acyltransferase (GLYAT) enzyme, are possible without departing from the scope of the appended claims.

The invention claimed is:

1. A method of improving the capacity of glycine-conjugation detoxification system, enhancing detoxification, or treating metabolic disorders and acute or chronic poisoning with xylene or aspirin in mammals due to enhancement of glycine conjugation comprising administering an effective amount of between 0.1 mg and 160 mg of water soluble enzymatically active recombinant human glycine N-acyltransferase E.C. number 2.3.13 (GLYAT E.C. number 2.3.13) per kilogram of body weight to a mammal in need thereof.

2. The method according to claim 1, wherein the GLYAT E.C. number 2.3.13 is prepared by:
 providing a suitable expression host;
 preparing a vector including a gene for expressing GLYAT E.C. number 2.3.13 in the expression host to form an expression plasmid;
 transforming the host with the expression plasmid to form an expression system;
 expressing the GLYAT E.C. number 2.3.13 gene in the expression system; and
 separating the expressed GLYAT E.C. number 2.3.13 from the expression system.

3. The method according to claim 2, wherein the step of separating the expressed GLYAT E.C. number 2.3.13 from the expression system includes the steps of separating the water soluble fraction of the expression system from the insoluble material and concentrating or lyophilizing the separated GLYAT E.C. number 2.3.13.

4. A method according to claim 2, wherein the expression host is selected from the group consisting of eukaryotic systems, prokaryotic systems, and archaeon systems.

5. A method according to claim 4, wherein the eukaryotic systems include yeast cell expression-, insect cell expression-, and mammalian cell expression systems; and wherein the prokaryotic systems include *Escherichia coli*.

6. A method according to claim 5, wherein, when the expression host is *Escherichia coli*, vectors are prepared to include genes for expressing GLYAT E.C. number 2.3.1.13 and chaperone proteins GroEL and GroES in the prokaryotic system expression host to form expression plasmids; and wherein the GLYAT E.C. number 2.3.1.13 and chaperone proteins are expressed in the expression system.

7. A method according to claim 6, including the further step of combining the separated expressed GLYAT E.C. number 2.3.1.13 with glycine.

8. A method according to claim 7, wherein the separated expressed GLYAT E.C. number 2.3.1.13 and glycine is combined with at least one inert pharmaceutically acceptable carrier or diluents in a dosage form selected from a group comprising tablet;

capsule; suspension; syrup; and a colloidal system that contains lipid-based submicron- and micron-sized structures; or the separated expressed GLYAT E.C. number 2.3.1.13 and glycine is fused to TAT (transactivator of transcriptions) peptide used as a membrane permeating agent; or the separated expressed GLYAT E.C. number 2.3.1.13 and glycine is provided in a suitable form for intradermal-; intramuscular-; intravenous-; or subcutaneous injection.

9. A method according to claim 1, wherein the metabolic disorders are any one or more of the conditions selected from the group consisting of organic acidemias selected from propionic acidemia, isovaleric acidemia and glutaric aciduria;

aminoacidurias selected from maple syrup urine disease and hyperglycinemia, and urea cycle disorders.

* * * * *